(12) United States Patent
Wagstaff

(10) Patent No.: US 8,642,017 B2
(45) Date of Patent: Feb. 4, 2014

(54) METHOD OF USING AND COMPOSITION FOR A FOAMING ORAL CLEANER

(75) Inventor: Robert K. Wagstaff, Springville, UT (US)

(73) Assignee: Orabrush, Inc., Provo, UT (US)

( * ) Notice: Subject to any disclaimer, the term of this patent is extended or adjusted under 35 U.S.C. 154(b) by 0 days.

(21) Appl. No.: 13/349,456

(22) Filed: Jan. 12, 2012

(65) Prior Publication Data

US 2012/0180806 A1    Jul. 19, 2012

Related U.S. Application Data

(60) Provisional application No. 61/432,466, filed on Jan. 13, 2011.

(51) Int. Cl.
    *A46B 17/08*    (2006.01)

(52) U.S. Cl.
    USPC .............. 424/50; 15/160; 15/111; 15/167.1

(58) Field of Classification Search
    None
    See application file for complete search history.

(56) References Cited

U.S. PATENT DOCUMENTS

| 6,792,642 | B2 | 9/2004 | Wagstaff | |
| 2003/0211053 | A1* | 11/2003 | Szeles et al. | 424/50 |
| 2006/0086048 | A1* | 4/2006 | Romley | 49/103 |

FOREIGN PATENT DOCUMENTS

| AU | B-30182/97 | * | 4/1998 |
| WO | WO 2009/102939 | * | 8/2009 |

OTHER PUBLICATIONS

Danser et al. "Tongue coating and tongue brushing: a literature review," International Journal of Dental Hygiene 1:151-158, 2003.*
TropiClean, Mint Foam, Gentle Foamer, Instant Fresh Breath, http://www.tropiclean.net/products/mint-foam.php, Feb. 2, 2012, 1 Pg.

* cited by examiner

*Primary Examiner* — Kortney L Klinkel
*Assistant Examiner* — Alissa Prosser
(74) *Attorney, Agent, or Firm* — Kirton McConkie; Brian Tucker

(57) ABSTRACT

Compositions for a foaming oral cleaner and related methods and products are disclosed. In one such method, a foaming oral cleaner may be dispensed onto a cleaning surface of a tongue cleaning device in a manner to foam the foaming oral cleaner. A surface of the tongue may be brushed using a tongue brush of the tongue cleaning device, thereby applying the foaming oral cleaner to the surface of the tongue. The brushing of the surface of the tongue can dislodge and loosen material on the surface of the tongue. The surface of the tongue can be scraped using a tongue scraper of the tongue cleaning device to scrape dislodged and loosened material from the surface of the tongue. The foaming oral cleaner may be a composition comprising water, a foaming agent, a sweetener, a flavoring agent, an antimicrobial agent comprising a biologically active enzyme, a preservative, and a coloring agent.

7 Claims, 6 Drawing Sheets

METHOD OF USING AND COMPOSITION FOR A FOAMING ORAL CLEANER

RELATED APPLICATIONS

This application claims the benefit under 35 U.S.C. §119(e) of U.S. Provisional Patent Application No. 61/432,466, filed Jan. 13, 2011, and titled "METHOD OF USING AND COMPOSITION FOR A FOAMING ORAL CLEANER," which is hereby incorporated herein by reference in its entirety.

TECHNICAL FIELD

The present disclosure relates to oral hygiene, and more specifically to methods and compositions for oral cleaning.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION OF PREFERRED EMBODIMENTS

Figures 1A, 1B, 1C:
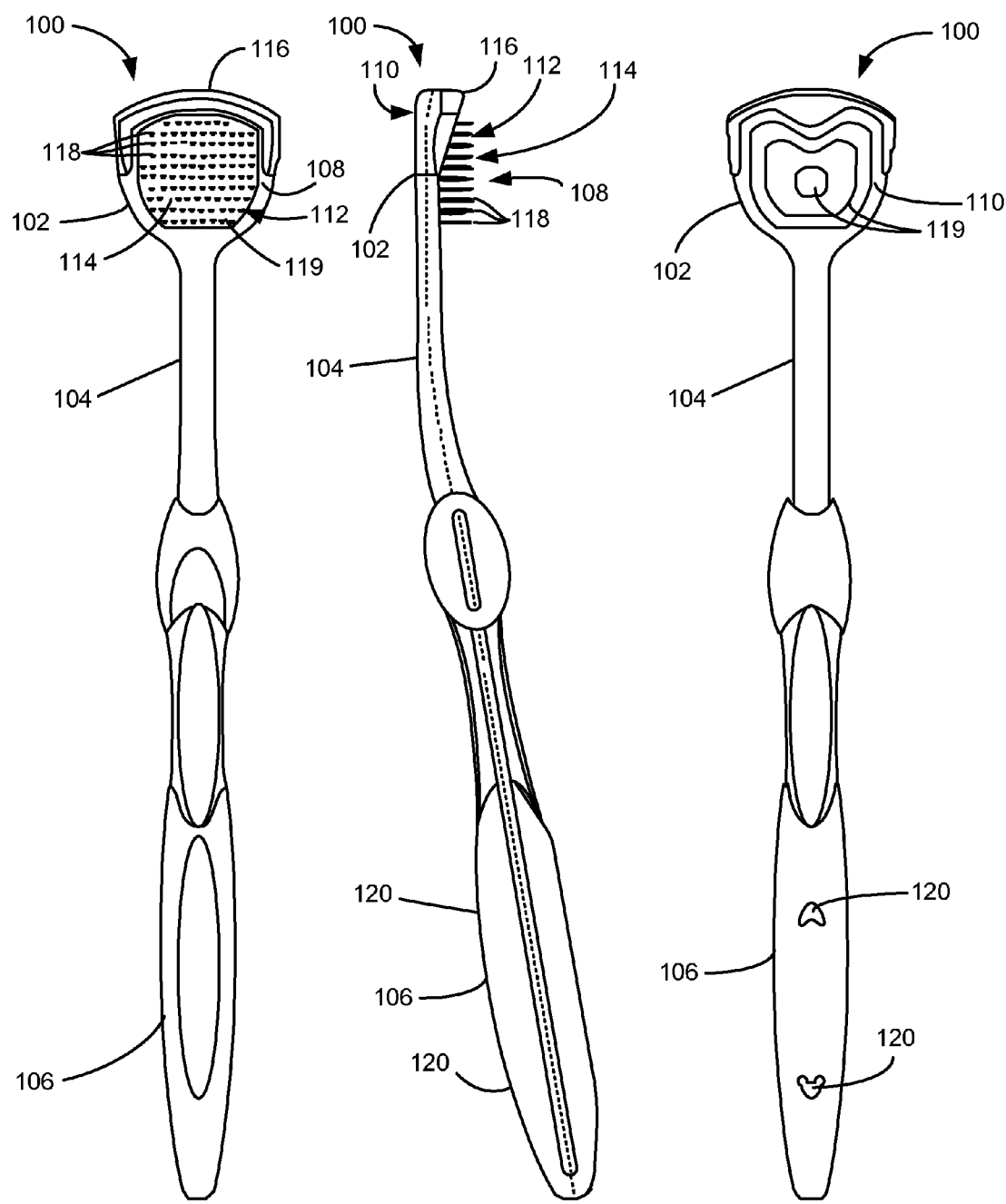
FIGS. 1A-1C are views of an embodiment of a tongue cleaning device that can be utilized in one or more methods of the present disclosure.

The present disclosure is directed to devices, methods, and compositions for oral hygiene, and specifically to cleaning the human mouth.

The primary cause of bad breath is due to bacteria living on the surface of the tongue. These bacteria produce odors. They also produce waste materials that are deposited on the tongue that further produce odors. Food debris can also produce odors. Controlling bad breath involves removing these bacteria, waste, debris, and other materials from the surface of the tongue.

Removal of bacteria, waste, debris, and other materials can be difficult due to the texture and shape of the surface of the tongue. The dorsal surface of the tongue is rough and covered with papillae, which are hair-like protrusions. The tongue also has many grooves, fissures, indentations, ducts, and other small openings where taste buds and salivary glands are positioned. These grooves, fissures, indentations, ducts, and other small openings collect food debris, waste materials, and other materials, which provide a comfortable breeding ground that attracts bacteria. Moreover, the roughness of the surface of the tongue presents challenges for cleaning the tongue because the bacteria, waste material, debris, and other materials are not easily removed from the small openings on the surface of the tongue.

A toothbrush is not an effective tongue cleaning implement. A toothbrush is shaped and configured to clean the relatively flat surfaces of the teeth. Specifically, the bristles of a toothbrush are relatively rigid and have flat tips configured to brush the surfaces of teeth. Thus, the bristles of a toothbrush are not properly shaped or configured to effectively access the grooves, fissures, indentations, ducts, and other small openings on the surface of the tongue.

Toothpaste and tooth gel are also not effective for cleaning the tongue because the pasty (or gel-like) consistency and can tend to collect in, and further clog, the small openings and indentations on the surface of the tongue, thereby exacerbating rather than ameliorating the problem.

The present disclosure provides compositions for cleaning the tongue and other soft tissue of the mouth, and methods of using the same. The composition may include an oral cleaner having a foaming agent that enables generation of foam prior to entry in the mouth and in a manner not requiring agitation in the mouth (such as by a repetitive brushing action). As used herein, the term "foam" indicates an emulsion-like two-phase system where the dispersed phase is gas or air as a collection of minute bubbles forming a frothy liquid substance. The term "foam" is also used as a verb to indicate formation or gathering of foam.

The present disclosure is also directed to methods of cleaning the human mouth, and specifically the tongue, using a foaming oral cleaner of the type disclosed.

The present disclosure is also directed to methods of using a foaming oral cleaner of the type disclosed, including foaming the oral cleaner prior to entry into the mouth and/or prior to agitation in the mouth.

Embodiments may be best understood by reference to the drawings, wherein like parts are designated by like numerals throughout. It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail.

FIGS. 1A-1C are views of an embodiment of a tongue cleaning device that can be utilized in one or more methods for cleaning the tongue of the present disclosure. FIG. 1A is a front view of a tongue cleaning device 100, according to one embodiment. FIG. 1B is side view of the tongue cleaning device 100 of FIG. 1A. FIG. 1C is a back view of the tongue cleaning device of FIG. 1A.

Referring collectively to FIGS. 1A-1C, the illustrated tongue cleaning device 100 is an elongated member that includes a head 102 at the distal end, a neck 104, and a handle 106 at the proximal end. The neck 104 may emanate from the handle 106. The head 102 has a front side 108 and a back side 110. The front side 108 includes a cleaning surface 112, which may comprise a tongue brush 114 and a tongue scraper 116. A user can brush the tongue with the tongue brush 114 to loosen bacteria, waste materials, food debris, and other materials from the surface of the tongue and then use the tongue scraper 116 to scrape away the loosened material.

The tongue brush 114 includes a plurality of bristles 118. The bristles may be tapered or cut to a point. The bristles 118 may be single-pointed, flexible, soft, individually mounted, non-tufted bristles. The bristles 118 may be configured to bend or arch slightly toward the handle 106 (or toward the proximal end), to improve access to the small openings on the surface of the tongue. As can be seen in FIG. 1, the bristles 118 can emanate from a supporting base or bristle base 119 configured to couple to the front surface of the head 102. In the illustrated embodiment, portions of the bristle base 119 may also pass through the head 102 to the back side 110, to secure the bristle base 119 and bristles 118 to the head 102. The bristles 118 and bristle base 119 may be formed of an elastic, flexible material, configured to give the bristles 118 a soft feel and to avoid damage or injury to the surface of the tongue. The bristles 118 are configured to reach down into the small openings and indentations of the tongue to loosen and dislodge bacteria, waste material, food debris, and other material entrapped in the small openings and indentations.

The tongue scraper 116 may comprise one or more tongue scraper blades that may be more rigid than the bristles 118 yet remain substantially flexible so as to not damage or injure the surface of the tongue.

The tongue cleaning device 100 illustrated in FIG. 1 may also have ridged finger grips 120 on the handle 106 to enhance handling and manipulation of the tongue cleaning device 100.

Other embodiments of a tongue cleaning device 100 are disclosed in U.S. Pat. No. 6,792,642, which is attached hereto as Appendix A. As can be appreciated, other embodiments of a tongue cleaning device may be used, such as a mechanical tongue cleaning device having a motor configured to automatically vibrate the head in a manner to produce a brushing action from back to front, or a travel tongue cleaning device that is foldable for easy storage and transport.

The tongue cleaning device 100 can be used to clean the tongue. A user can grasp the handle 106 and insert the head 102 into the mouth with the cleaning surface 112 of the head 102 against the tongue. A firm but gentle brushing action against the tongue, from front to back and from back to front, can loosen bacteria, debris and other material from the surface of the tongue. The bristles 118 are shaped and configured to gently penetrate into the small openings on the surface of the tongue to dislodge and discharge bacteria, debris, and other material within. The soft, flexible bristles 118 of the tongue cleaning device 100 are configured to bend and weave to access the small openings on the surface of the tongue.

After one or more back and forth brushes with the tongue brush 114, the tongue scraper 116 can be used to scrape the dislodged and loosened bacteria, debris and other material off the surface of the tongue. In particular, the head 102 can be positioned near the back of the tongue (i.e., toward the throat), the handle 106 can be tilted slightly upward to cause the blade of the tongue scraper 116 to engage the surface of the tongue toward the back of the tongue, and the handle 106 can be pulled forward to drag the tongue scraper 116 along the surface of the tongue. An appropriate tilt angle of the handle 106 can allow a blade of the tongue scraper 116 to be positioned against the tongue, as low as, or lower than the bristles 118 of the tongue cleaning brush, flush with the surface of the tongue. Otherwise, contact of the bristles 118 of the tongue brush 114 with the surface of the tongue may limit access of the tongue scraper 116 to the surface of the tongue.

The efficacy of the tongue cleaning device 100 can be improved by utilizing a foaming oral cleaner, according to an embodiment of the present disclosure. A foaming oral cleaner can penetrate the small openings of the surface of the tongue and provide a lubricant that can enhance dislodgment of bacteria, waste materials, food debris, and other materials. The bristles 118 of the tongue cleaning device 100 are configured to work in a water or water-like environment. Water, or a water-like solution, can function as a lubricant to allow the bristles 118 to more easily bend and weave to access the small openings on the surface of the tongue. The foaming oral cleaner can be rapidly reduced to a water-like solution in the mouth, which enhances the action of the bristles 118. Moreover, the water-like solution that results from reduction of the foaming oral cleaner can function as a solvent that dissolves the bacteria, waste materials, food debris, and other materials that are loosened and dislodged by the bristles 118, allowing easier discharge from the mouth.

A foaming oral cleaner, according to an embodiment of the present disclosure, can also function as a delivery medium for an antimicrobial substance. The antimicrobial substance can kill bacteria on the tongue, which facilitates dislodgment of bacteria during cleaning and further enhances efficacy of the tongue cleaning device. The antimicrobial substance also helps prevent re-growth of bacteria, thereby prolonging the effects of the tongue cleaning.

A foaming oral cleaner, according to an embodiment of the present disclosure, can also function as a delivery medium for a flavor and/or scent that can enhance the cleaning experience and leave a pleasant odor in the mouth.

A water-like substance is difficult to effectively apply to the cleaning surface of a tongue cleaning device. A water or water-like substance may flow and drip off the cleaning surface of the tongue cleaning device. Similarly, a water or water-like substance may flow and drip off the surface of the tongue when applied directly to the tongue. Thus, an antimicrobial substance and/or a flavor may not be effectively dispensed to the surface of the tongue in a water-like substance, at least not in conjunction with a tongue cleaning device. A foaming oral cleaner, according to the present disclosure, can be foamed to have a consistency that can be applied to a tongue cleaning device, for corresponding application to the surface of the tongue. The foam provides a relatively viscous consistency that can be temporarily affixed to a tongue cleaning device long enough to position the foaming oral cleaner in the mouth and on the surface of the tongue. Once in the mouth and/or on the surface of the tongue, the foam can also be rapidly reduced to a water-like solution, having desirable characteristics for cleaning the grooves, fissures, indentations, ducts, and other small openings of the tongue.

A foaming oral cleaner, according to an embodiment of the present disclosure, may comprise a foaming agent, a sweetener, a surfactant, a flavoring or scented agent, an antimicrobial agent, an anti-bacterial agent, an anti-oxidant, an anti-caries agent, a coloring agent, a thickening agent, a preservative, a disinfectant, water and a pH-adjusting agent. A combination and/or blend of these constituents may be used for the foaming oral cleaner, and a single ingredient may act in multiple modes.

In an embodiment, the foaming oral cleaner may comprise xylitol, a sweetener with antimicrobial properties. In another embodiment, the sweetener may comprise stevia. In one embodiment, the sweetener may be present in a weight percentage of between about 0.1 to about 10 percent.

In an embodiment, the foaming oral cleaner may comprise at least one surfactant, which may be ionic or non-ionic. For example, sodium lauryl sulfate is an ionic surfactant and polysorbate 80 is a non-ionic surfactant. Other examples of surfactants include polysorbate 20, PEG-40 hydrogenated castor oil, cocamidopropyl betaine, sodium lauroyl sarcosinate, and poloxamer 407. The surfactant may also be a detergent and/or an emulsifying agent. In an embodiment, the surfactant may comprise cetyl hydroxyethylcellulose. In an embodiment, a surfactant may be present in a weight percentage of between about 0.1 to about 2.5 percent.

In an embodiment, the foaming oral cleaner may comprise at least one foaming agent. The foaming agent may be, but is not necessarily, a surfactant. Exemplary foaming agents include cellulose gum and sorbitol. In one embodiment, a foaming agent may be present in a weight percentage of between about 0.1 to about 4.0 percent.

In an embodiment, the foaming oral cleaner may comprise at least one antimicrobial agent, anti-bacterial agent, anti-oxidant, or anti-caries agent. For example, a licorice extract, a biologically active enzyme or group of enzymes (such as Selectobac™ or Salzyme™), lutein, aloe vera, or cetylpyridinium chloride may be used. In one embodiment, at least one antimicrobial agent, anti-bacterial agent, anti-oxidant, or anti-caries agent may be present in a weight percentage of between about 0.01 to about 1.0 percent each.

In an embodiment, the group of enzymes may be selected from at least one of lysozyme, amylase, amyloglucosidase, glucoxidase, Peptizyme® known generically as serrapeptase, papain and lactoferrin. In another embodiment, the group of enzymes may be Orazyme™.

Enzymes may be added to an oral cleaner to aid in the formation and/or growth of bacterial cultures that do not produce bad breath or disease, or to reduce the formation and/or growth of bacteria that do produce bad breath or disease. Use of the inventive oral cleaner may control bad breath, resulting in a user no longer needing mouth fresheners such as chewing gum, breath mints, and mouthwashes.

In an embodiment, the foaming oral cleaner may comprise a flavoring or scented agent, for example, peppermint oil, mint, fruits, and other flavors. The flavoring or scented agent may be organic. In one embodiment, a flavoring or scented agent may be present in a weight percentage of between about 0.01 to about 1.0 percent.

In an embodiment, the foaming oral cleaner may comprise a pH-adjusting agent. For example, sodium hydroxide, sodium hydrogen carbonate, or sodium phosphate may be used to adjust the pH of the cleaner. In one embodiment, a pH-adjusting agent may be present in a weight percentage of between about 0.02 to about 4.0 percent.

In an embodiment, the foaming oral cleaner may comprise a thickening agent, for example, glycerol (glycerin), cellulose gum, propanediol, or sorbitol. In one embodiment, a thickening agent may be present in a weight percentage of between about 0.01 to about 0.8 percent.

In an embodiment, the foaming oral cleaner may comprise a preservative, for example, ethanol, or benzoic acid. In one embodiment, a preservative may be present in a weight percentage of between about 1.0 to about 9.0 percent.

In an embodiment, the foaming oral cleaner may comprise a disinfectant, for example, an alcohol. In one embodiment, a disinfectant may be present in a weight percentage of between about 0.5 to about 9.0 percent.

In an embodiment, the foaming oral cleaner may comprise a coloring agent, for example, FD & C Blue #1. In one embodiment, a coloring agent may be present in a weight percentage of between about 0.001 to about 0.08 percent.

In an embodiment, the foaming oral cleaner may comprise water. In one embodiment, water may be present in a weight percentage of between about 50 to about 95 percent.

In an embodiment, the foaming oral cleaner may comprise a vitamin or nutritive supplement, for example, zinc gluconate. In one embodiment, a vitamin or nutritive supplement may be present in a weight percentage of between about 0.001 to about 0.3 percent.

In an embodiment, the foaming oral cleaner comprises water, at least one foaming agent, at least one sweetener, at least one flavoring agent, at least one antimicrobial agent comprising a biologically active enzyme, at least one preservative, and at least one coloring agent.

In an embodiment, the biologically active enzyme comprises at least one of lysozyme, amylase, amyloglucosidase, glucoxidase, Peptizyme® known generically as serrapeptase, papain and lactoferrin.

The biologically active enzyme may comprise a group of enzymes, or be a mixture or combination of enzymes, including mixtures or combinations of lysozyme, amylase, amyloglucosidase, glucoxidase, Peptizyme® known generically as serrapeptase, papain and lactoferrin.

In another embodiment, the foaming oral cleaner may comprise water, denatured ethanol, xylitol, stevia, sodium lauroyl sarcosinate, glycerin, polysorbate 80, cetyl hydroxyethylcellulose, peppermint oil and sodium hydroxide.

In yet another embodiment, the foaming oral cleaner comprises water, sorbitol, xylitol, propanediol, cellulose gum, poloxamer 407, benzoic acid, Selectobac™, an organic flavoring agent, Salzyme™, aloe vera, sodium phosphate and zinc gluconate.

The foaming oral cleaner may have a range of viscosities in its foamed state. Viscosity may be measured in centipoises (cP). In one embodiment, the viscosity of the foaming oral cleaner may be between about 1 and 25,000 cP. For example, the viscosity of the cleaner may be between about 1 and 5,000 cP. Alternatively, the viscosity of the cleaner may be between about 1 and 1,000 cP or between about 1 and 50 cP.

The foaming oral cleaner may have a range of densities in its foamed state. Density may be measured in kilograms per cubic meter ($kg/m^3$). In some embodiments, the density of the foaming oral cleaner may be less than about 200 $kg/m^3$. In some such embodiments, the density of the cleaner may be less than about 175 $kg/m^3$. In some such embodiments, the density of the cleaner may be between about 110 $kg/m^3$ and about 135 $kg/m^3$.

Figure 2:
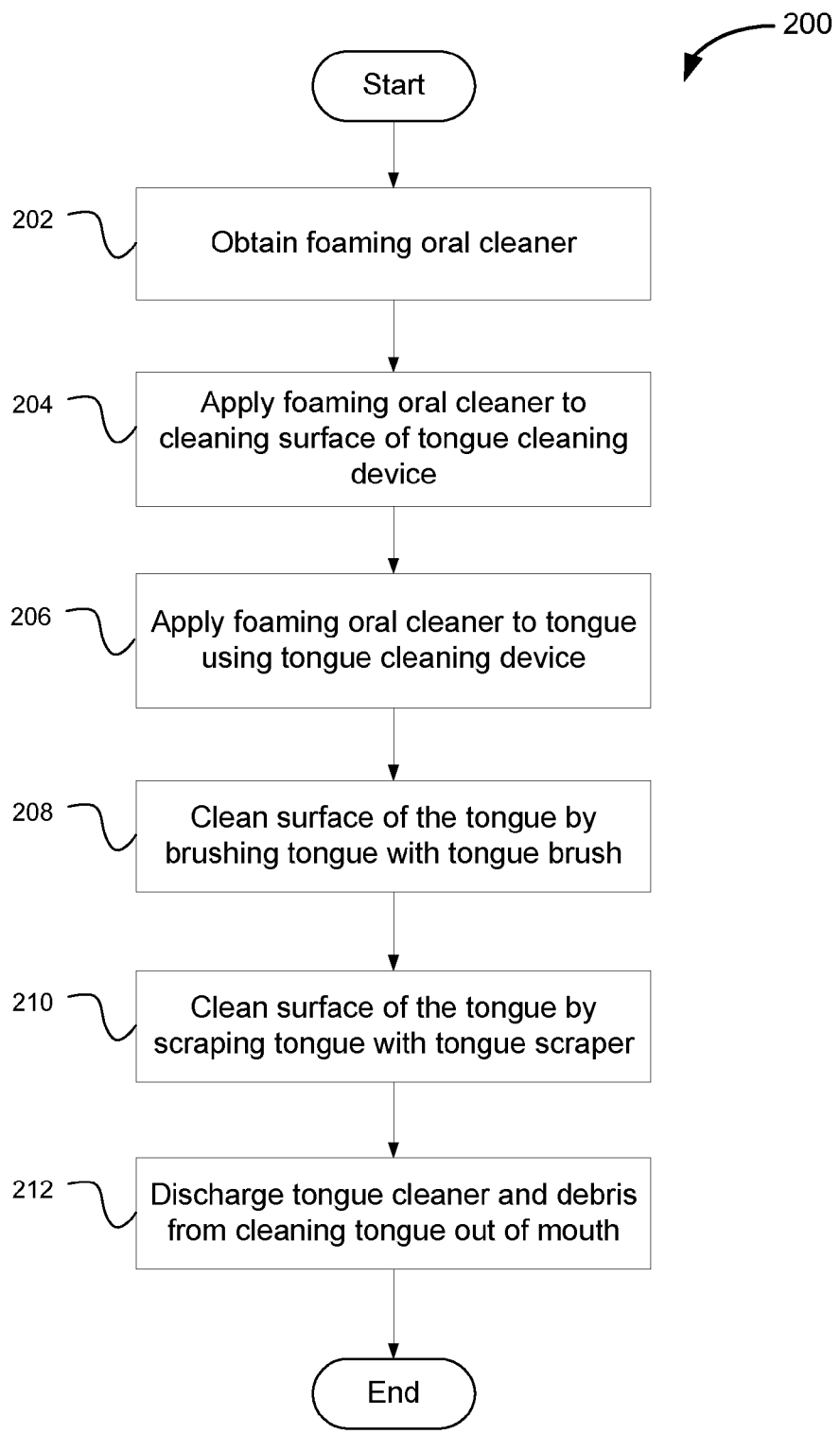
FIG. 2 is flow diagram of a method of cleaning the tongue, according to an embodiment of the present disclosure.

FIG. 2 is flow diagram 200 of a method of cleaning the tongue, according to an embodiment of the present disclosure. A user obtains 202 a foaming oral cleaner, such as a foaming oral cleaner as previously described. The foaming oral cleaner can be dispensed or otherwise applied 204 to the cleaning surface of a cleaning device (e.g., to the bristles of a tongue brush and/or a blade of a tongue scraper), such as the tongue cleaning device 100 of FIG. 1. The foaming oral cleaner can be dispensed or otherwise applied to the tongue cleaning device in a manner to produce a foam on the cleaning surface of the tongue cleaning device, prior to the tongue cleaning device and foaming oral cleaner being positioned in the mouth or on the tongue. For example, the foaming oral cleaner can be dispensed using a pump mechanism configured to pump the solution from a bottle. The pump mechanism may further provide an agitation to concurrently foam the foaming oral cleaner as it is applied to the tongue cleaning device. As another example, the foaming oral cleaner may be dispensed from an aerosol can, similar to shaving cream or whipped cream. As can be appreciated, other methods of dispensing the foaming oral cleaner are possible such as using a Venturi system to draw foaming oral cleaner from a storage container to mix with a stream of water and form a foam during application.

With the foaming oral cleaner appropriately applied 204 on the cleaning surface of the tongue cleaning device, the user can use the tongue cleaning device to apply 206 the foaming oral cleaner to the surface of the tongue. The user can then use the tongue cleaning device to clean the tongue, as described above, using a tongue brush to brush 208 the surface of the tongue and a tongue scraper to scrape 210 any dislodged or loosened material from the surface of the tongue. Moreover, a brushing action with the tongue cleaning device can function to work the foaming oral cleaner into the grooves, fissures, indentations, ducts, and other small openings on the surface of the tongue. The foaming oral cleaner may be quickly reduced to a water-like solution that functions to lubricate and improve the cleaning efficacy of the bristles of the tongue cleaning device and to dissolve the bacteria, waste material, food debris, and other materials loosened and dislodged from the surface of the tongue into a liquid solution.

After cleaning the tongue, the user can spit out or otherwise discharge 212 any remaining oral cleaner and/or solution of bacteria, waste material, food debris, and other materials loosened and dislodged from the surface of the tongue and dissolved in the reduced foaming oral cleaner.

Figure 3:
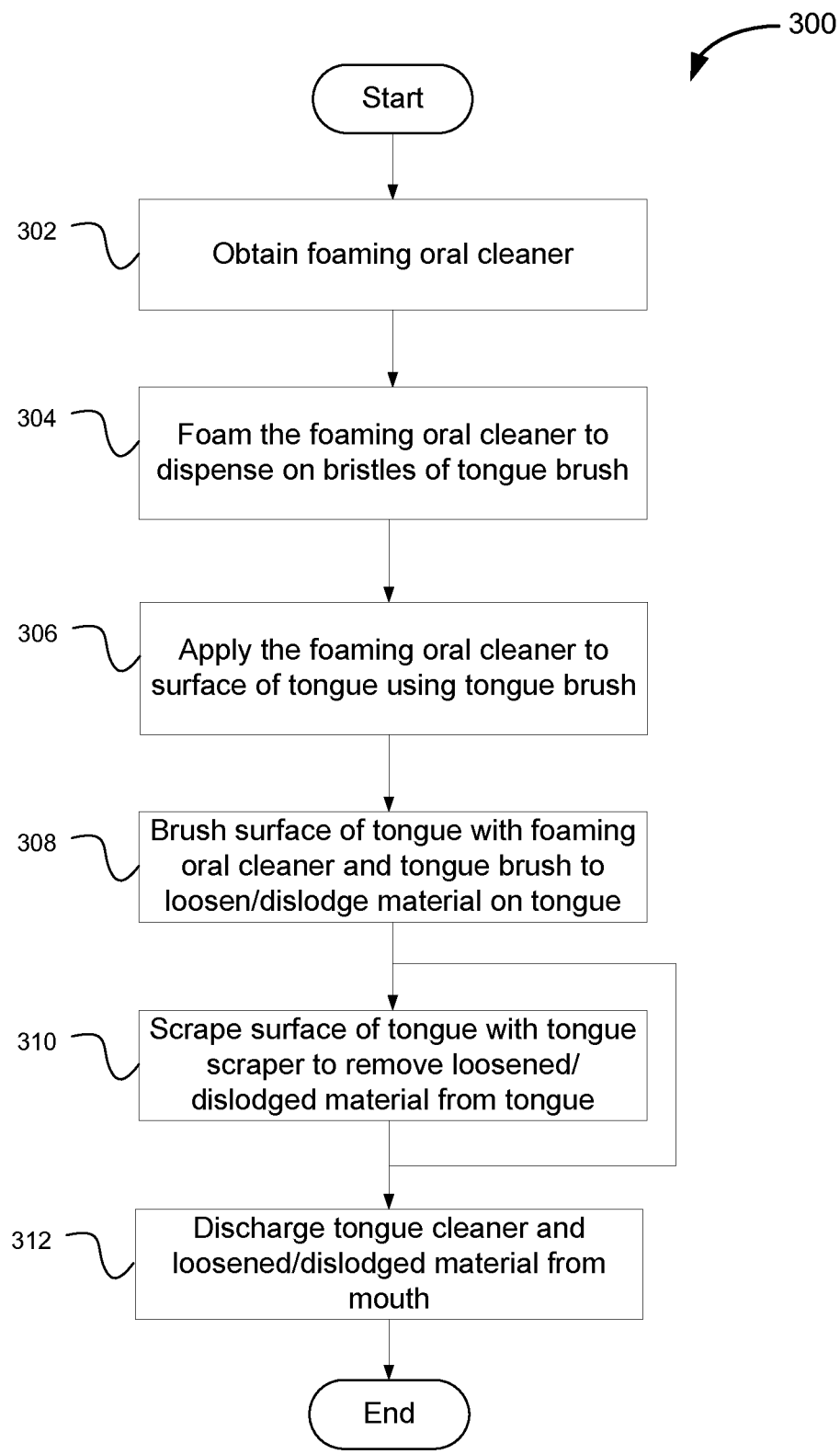
FIG. 3 is a flow diagram of a method for using a foaming oral cleaner, according to an embodiment of the present disclosure.

FIG. 3 is a flow diagram 300 of a method for using a foaming oral cleaner to clean the tongue, according to another embodiment of the present disclosure. A user may obtain 302 a foaming oral cleaner, such as a foaming oral cleaner as previously described. The user then foams 304 the foaming oral cleaner to dispense it on the bristles of a tongue brush, such as the tongue cleaning device 100 of FIG. 1. The foaming oral cleaner can be dispensed or otherwise applied to the tongue cleaning device in a manner to produce a foam on the cleaning surface of the tongue brush. The step of foaming 304 the cleaner may be accomplished prior to the user inserting the tongue brush and/or the cleaner into the mouth.

Foaming 304 the cleaner may comprise increasing the quantity of gas (or air) in the substance to decrease the density and/or increase the viscosity of the foaming oral cleaner. As explained previously, foaming 304 the cleaner may be accomplished, for example, by a mechanical pump that pumps the foaming oral cleaner from a bottle and concurrently agitates or otherwise injects gas (or air) into the cleaner to increase or otherwise enhance the collection of minute bubbles and a frothiness of the foaming oral cleaner. In another embodiment, foaming 304 the cleaner may be accomplished by dispensing the cleaner from an aerosol can configured to concurrently agitate or otherwise inject gas into the cleaner as it is dispensed. As can be appreciated, other methods of foaming the cleaner are possible, such as a Venturi system as described above.

The user can use the tongue cleaning device to apply 306 the foaming oral cleaner to the surface of the tongue. The user can then use the tongue cleaning device to clean the tongue. Specifically, the user can brush 308 the surface of the tongue with the foaming oral cleaner and tongue brush to loosen and/or dislodge bacteria, waste material, food debris, and other materials from the surface of the tongue. The foaming oral cleaner and/or the tongue brush clean the grooves, fissures, indentations, ducts, and other small openings on the surface of the tongue. The foaming oral cleaner may be quickly reduced to a water-like solution that functions to lubricate and improve the cleaning efficacy of the bristles of a tongue cleaning device and to dissolve the bacteria, waste material, food debris, and other materials loosened and dislodged from the surface of the tongue. The user can scrape 310 the surface of the tongue with a tongue scraper to remove loosened/dislodged material from the tongue. The user can discharge 312 tongue cleaner and loosened/dislodged material from the mouth by spitting.

Figure 4:
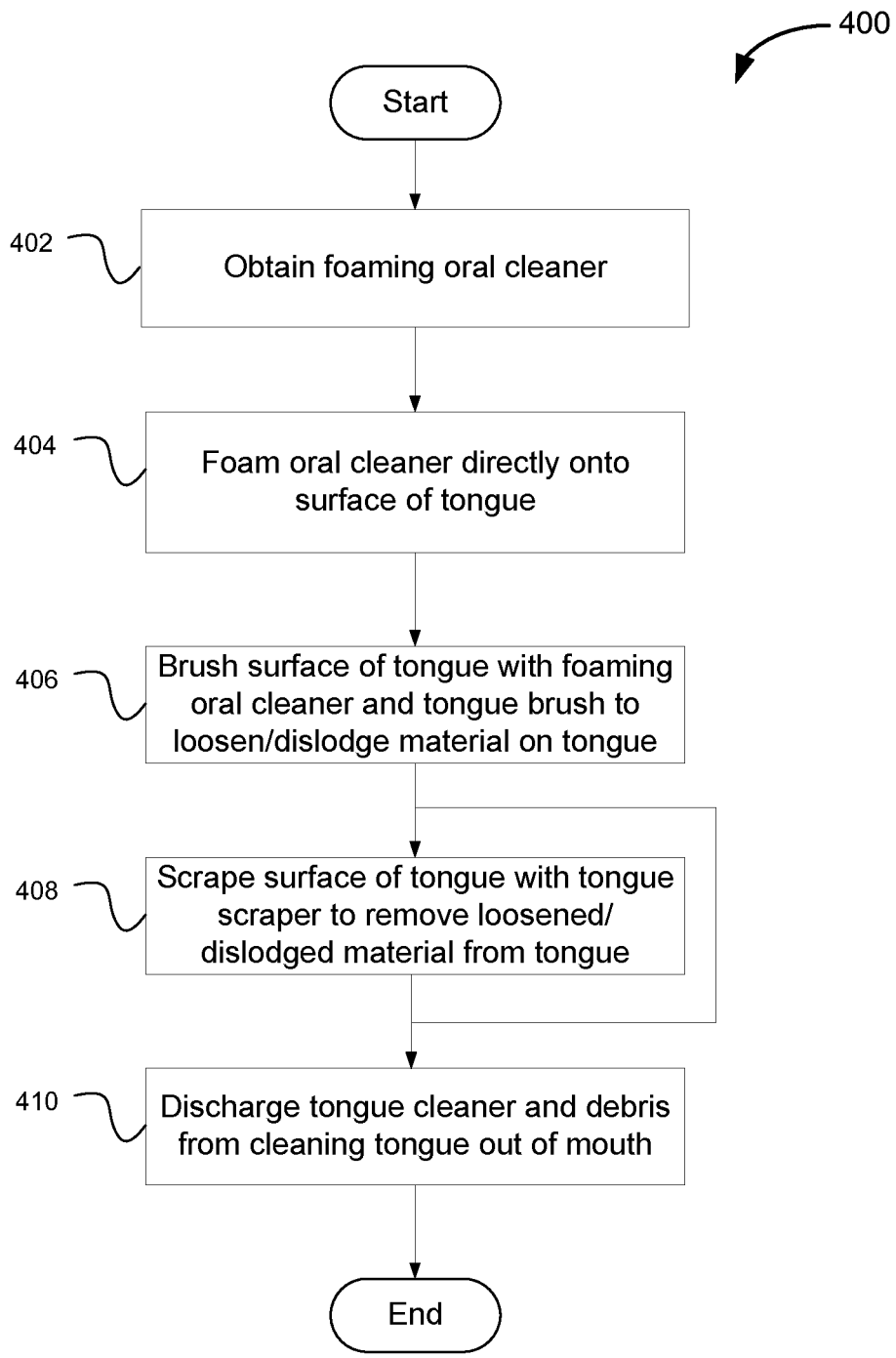
FIG. 4 is a flow diagram of a method of cleaning the tongue, according to another embodiment of the present disclosure.

FIG. 4 is a flow diagram 400 of a method for using a foaming oral cleaner to clean the tongue according to another embodiment of the present disclosure. A user may obtain 402 a foaming oral cleaner, such as a foaming oral cleaner as previously described. The user may then foam 404 the foaming oral cleaner to apply it directly to the tongue. Foaming 404 the cleaner may comprise increasing the quantity of gas (or air) in the substance to decrease the density and/or increase the viscosity of the foaming oral cleaner. As explained previously, foaming 404 the cleaner may be accomplished, for example, by a mechanical pump that pumps the foaming oral cleaner from a bottle and concurrently agitates or otherwise injects gas (or air) into the cleaner to increase or otherwise enhance the collection of minute bubbles and a frothiness of the foaming oral cleaner. In another embodiment, foaming 404 the cleaner may be accomplished by dispensing the cleaner from an aerosol can configured to concurrently agitate or otherwise inject gas into the cleaner as it is dispensed. As can be appreciated, other methods of foaming the cleaner are possible, such as a Venturi system as described above.

The user can then use the tongue cleaning device to spread the foaming oral cleaner and/or clean the tongue. Specifically, the user can brush 406 the surface of the tongue with the foaming oral cleaner and tongue brush to loosen and/or dislodge bacteria, waste material, food debris, and other materials from the surface of the tongue. The foaming oral cleaner and/or the tongue brush clean the grooves, fissures, indentations, ducts, and other small openings on the surface of the tongue. The foaming oral cleaner is quickly reduced to a water-like solution that functions to lubricate and improve the cleaning efficacy of the bristles of a tongue cleaning device and to dissolve the bacteria, waste material, food debris, and other materials loosened and dislodged from the surface of the tongue. The user can optionally scrape 408 the surface of the tongue with a tongue scraper to remove loosened/dislodged material from the tongue. The user can discharge 410 tongue cleaner and loosened/dislodged material from the mouth by spitting.

Figure 5:
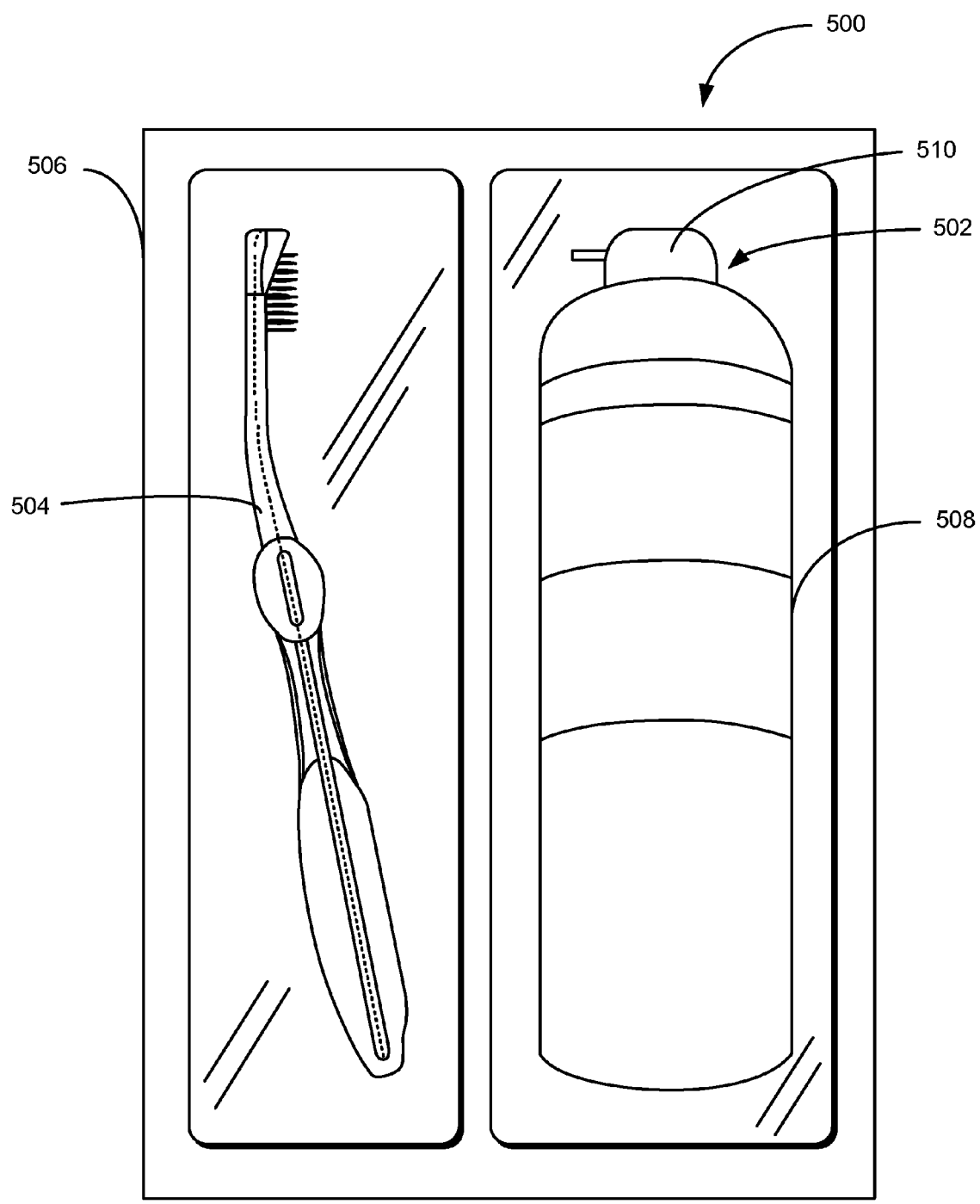
FIG. 5 is a kit for cleaning the tongue, according to an embodiment of the present disclosure.

FIG. 5 is a kit 500 for cleaning the tongue, according to an embodiment of the present disclosure. The kit 500 may include a foaming oral tongue cleaner 502 and a tongue cleaning device 504 packaged together in a packaging 506. The foaming oral cleaner 502 may be provided in a bottle 508 with a pump mechanism 510. As can be appreciated, in another embodiment, the foaming oral tongue cleaner 502 may be provided in an aerosol can or other dispensing container.

Figure 6:
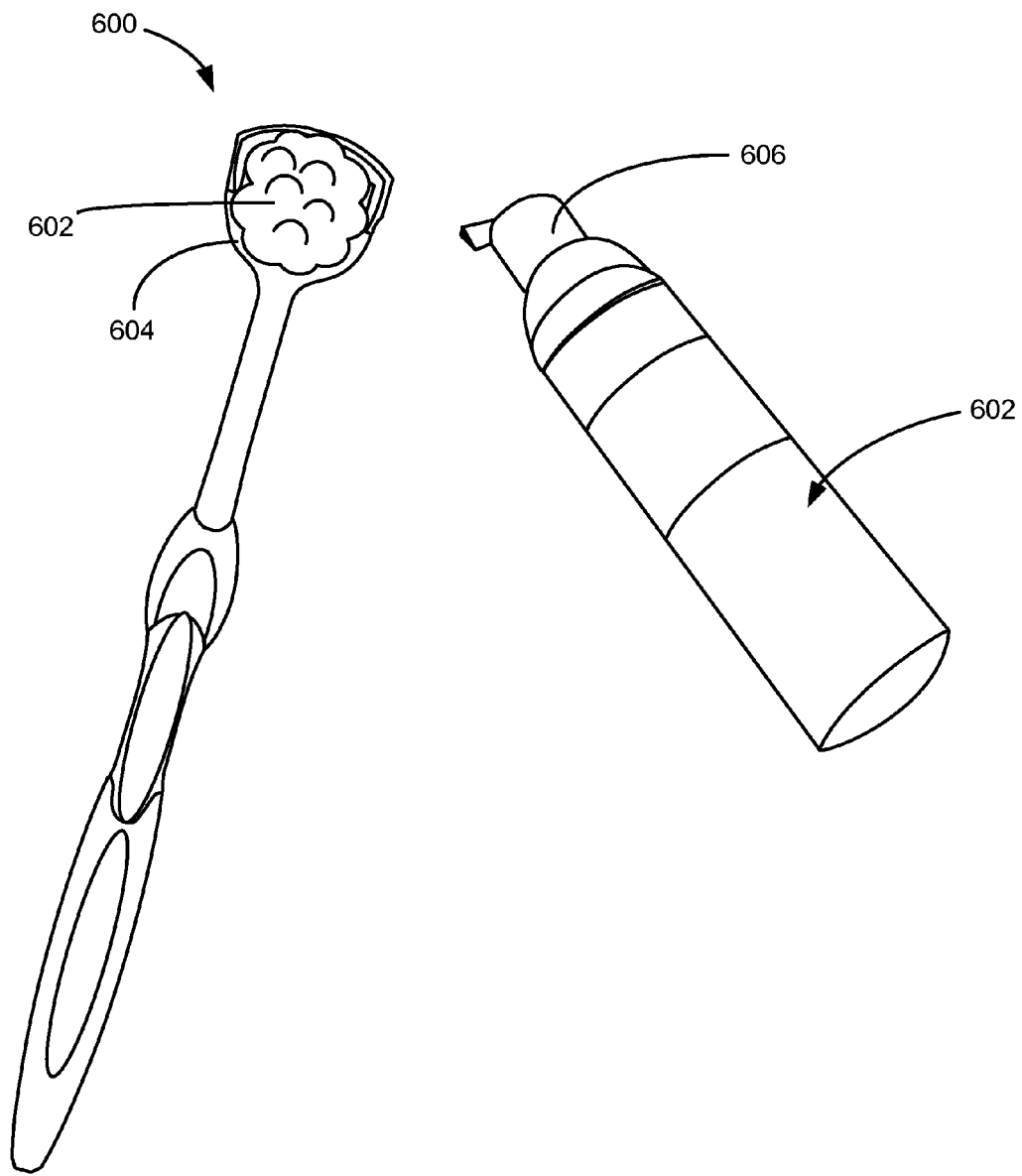
FIG. 6 is a perspective view of foaming oral cleaner deposited on a tongue cleaning device, according to an embodiment of the present disclosure.

FIG. 6 is a perspective view of a foaming oral cleaner 602 that is foamed and deposited on a tongue cleaning device 600, according to an embodiment of the present disclosure. The foaming oral cleaner 602 may be foamed using a mechanical pump 606 prior to insertion into the mouth and may be deposited on the bristles of a tongue brush 604 of the tongue cleaning device 600.

As can be appreciated, in another embodiment, the foaming oral cleaner 602 may be foamed or otherwise applied directly onto the surface of the tongue. Then the tongue brush 604 can be used to distribute the foamed oral cleaner 602 on the surface of the tongue in order to clean the surface of the tongue.

In still another embodiment, the foaming oral cleaner may be applied directly to the surface of the tongue and the user may simply swish the foaming oral cleaner around in the mouth as a mouthwash replacement. Although cleaning action of the bristles of a tongue brush may not be present, the foaming oral cleaner may still be effective to penetrate the small openings and indentations of the tongue to loosen and dislodge bacteria, waste material, food debris, and other material entrapped in the small openings and indentations.

Those having skill in the art will understand from the disclosure herein that many changes may be made to the details of the above-described embodiments without departing from the underlying principles of the invention. The scope of the present invention should, therefore, be determined only by the following claims.

I claim:

1. A method of applying a liquid cleaner to the surface of the tongue to clean the tongue comprising:

obtaining an oral cleaner comprising water, poloxamer 407 as a foaming agent, a sweetener, a flavoring agent, an antimicrobial agent, a preservative, and a coloring agent, wherein the oral cleaner is in liquid form prior to being dispensed from a container, converts to a foam while being dispensed, and returns to a liquid upon being placed on the tongue, the oral cleaner further containing a biologically active enzyme for breaking down material contained within the grooves in the surface of the tongue, the biologically active enzyme comprising one or more enzymes selected from the group consisting of lysozyme, amylase, amylglucosidase, glucoxidase, serrapeptase, papain, and lactoferrin;

dispensing the oral cleaner onto a cleaning surface of a tongue cleaning device in a manner to foam the oral cleaner on the cleaning surface of the tongue cleaning device;

applying the foamed oral cleaner on the surface of the tongue to cause the foamed oral cleaner to reduce to a liquid form upon contacting the surface of the tongue and flow into the grooves in the surface of the tongue thereby enhancing contact between the oral cleaner and material contained within the grooves;

brushing the surface of the tongue using a tongue brush of the tongue cleaning device to dislodge and loosen material from within the grooves in the surface of the tongue; and scraping the surface of the tongue using a tongue scraper of the tongue cleaning device to scrape dislodged and loosened material from the surface of the tongue.

2. The method of claim 1, wherein the foaming oral cleaner is dispensed from an aerosol can.

3. The method of claim 1, wherein the cleaning device is a tongue brush configured to loosen and dislodge material on the surface of the tongue to clean the surface of the tongue, the tongue brush comprising:

a handle at a proximal end;

a neck emanating from the handle; and a head at a distal end, the head including a front side and a back side, the front side having a cleaning surface comprising;

a tongue brush formed of a plurality of bristles that are tapered to a point, and a tongue scraper positioned distal to and adjacent to the tongue brush.

4. The method of claim 1, wherein applying the foaming oral cleaner to the surface of the tongue comprises working the foaming oral cleaner into grooves, fissures, indentations, ducts, and other small openings on the surface of the tongue to dislodge and loosen material on the surface of the tongue.

5. The method of claim 1, further comprising discharging from a mouth a solution comprising the oral cleaner and the material loosened and dislodged from the surface of the tongue.

6. The method of claim 1, wherein the material loosened and dislodged from the tongue comprises at least one of bacteria, waste materials, and food debris.

7. The method of claim 1, wherein foaming the foaming oral cleaner comprises increasing a quantity of gas in the foaming oral cleaner to decrease a density of the foaming oral cleaner and to increase a viscosity of the foaming oral cleaner.

* * * * *